United States Patent
Kraemer

(10) Patent No.: US 7,222,381 B2
(45) Date of Patent: May 29, 2007

(54) ELECTRIC TOOTHBRUSH WITH A REPLACEABLE HEAD SECTION

(75) Inventor: Hans Kraemer, Buehl (DE)

(73) Assignee: GlaxoSmithKline Consumer Healthcare GmbH & Co KG, Buehl (DE)

( * ) Notice: Subject to any disclaimer, the term of this patent is extended or adjusted under 35 U.S.C. 154(b) by 518 days.

(21) Appl. No.: 10/258,655

(22) PCT Filed: Apr. 24, 2001

(86) PCT No.: PCT/EP01/04604

§ 371 (c)(1),
(2), (4) Date: Mar. 10, 2003

(87) PCT Pub. No.: WO01/82826

PCT Pub. Date: Nov. 8, 2001

(65) Prior Publication Data

US 2004/0016067 A1  Jan. 29, 2004

(30) Foreign Application Priority Data

Apr. 27, 2000 (GB) .................... 0010115.4

(51) Int. Cl.
*A61C 17/22* (2006.01)
(52) U.S. Cl. .......................... 15/22.1; 15/28
(58) Field of Classification Search ........ 15/22.1–22.4, 15/23, 28
See application file for complete search history.

(56) References Cited

U.S. PATENT DOCUMENTS

| | | | | |
|---|---|---|---|---|
| 1,833,967 A | * | 12/1931 | Groff, Jr. .................. | 15/23 |
| 2,275,247 A | * | 3/1942 | Cavanagh .................. | 15/23 |
| 3,158,884 A | * | 12/1964 | Oscar ..................... | 15/23 |
| 3,195,537 A | * | 7/1965 | Blasi ..................... | 601/114 |
| 3,551,932 A | | 1/1971 | Grossman | |
| 4,603,448 A | * | 8/1986 | Middleton et al. ......... | 15/22.1 |
| 4,827,552 A | * | 5/1989 | Bojar et al. ............. | 15/28 |
| 5,617,601 A | * | 4/1997 | McDougall ............... | 15/22.1 |

FOREIGN PATENT DOCUMENTS

| | | | |
|---|---|---|---|
| CH | 399415 | | 9/1965 |
| DE | 19508932 | * | 9/1996 |
| EP | 488971 | * | 6/1992 |
| GB | 2278537 | * | 12/1994 |
| JP | 8-224126 | * | 9/1996 |
| JP | 08 299372 | | 11/1996 |
| JP | 8-322641 | * | 12/1996 |
| WO | WO98/12947 | | 4/1998 |

* cited by examiner

*Primary Examiner*—Mark Spisich
(74) *Attorney, Agent, or Firm*—Nora Stein-Fernandez; Theodore F. Furman; Charles M. Kinzig

(57) ABSTRACT

An electrically driven toothbrush having a replaceable head section with a plug part which is engageable with a socket in its handle to connect its driveable head to its motor in the handle. The head section has a resiliently deformable end surface, and there is an engaging concavity and convexity in the respective meeting end surfaces of the plug part and the socket. The concavity and convexity engage to facilitate locking together of the head and handle. A separate replaceable head section for such a toothbrush is also provided.

16 Claims, 7 Drawing Sheets

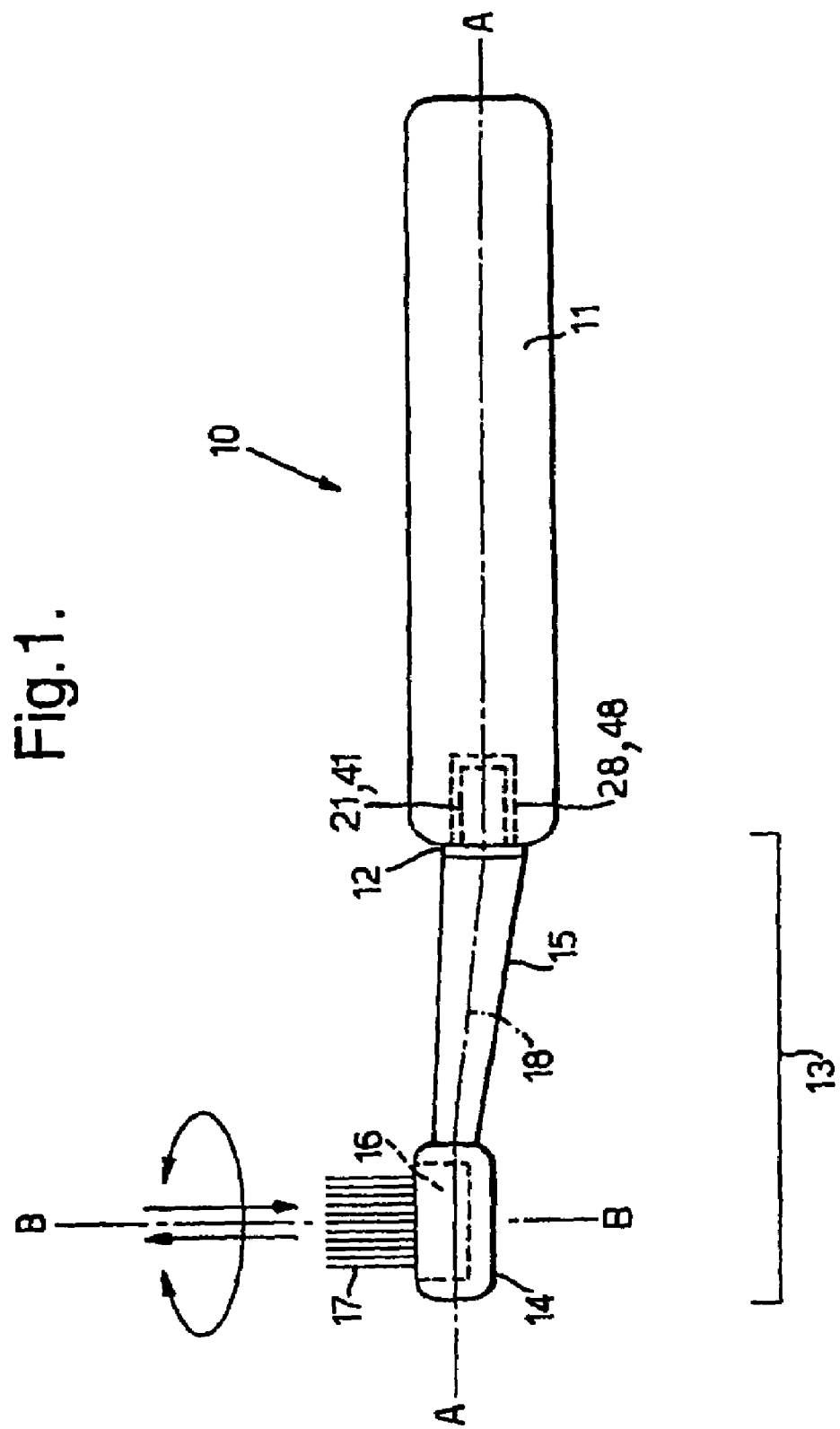

TO FIG.4C.

FROM FIG.4B.

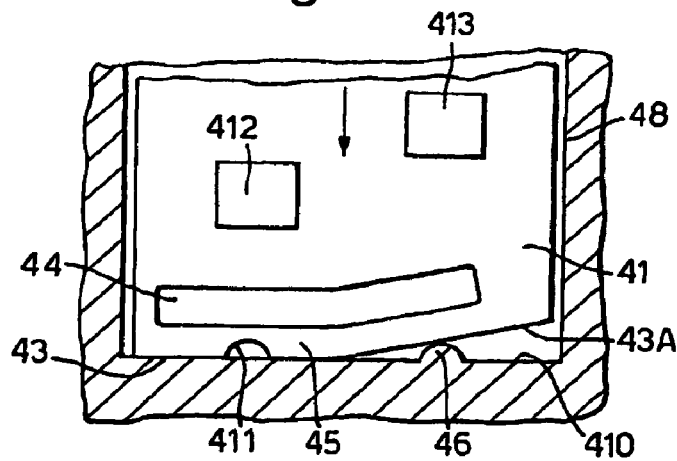
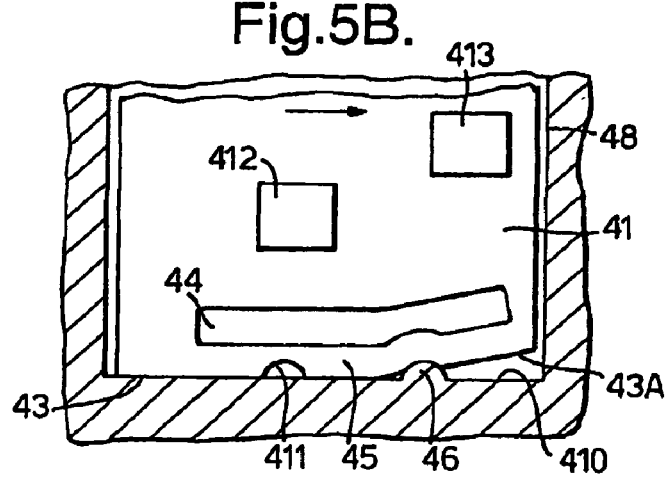
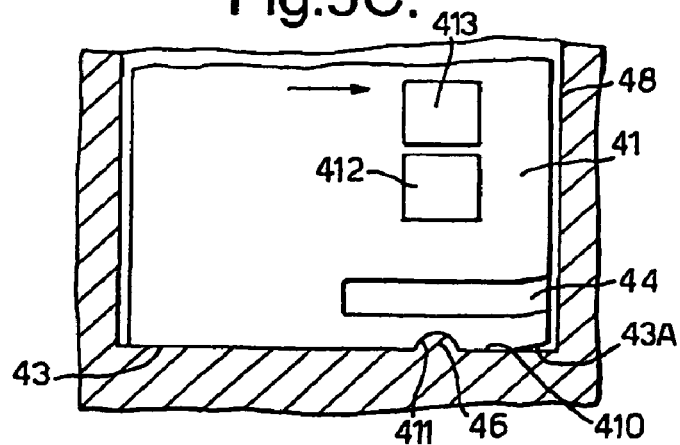

ELECTRIC TOOTHBRUSH WITH A REPLACEABLE HEAD SECTION

This invention relates to toothbrushes. In particular the invention relates to electric toothbrushes which comprise a handle containing an electric drive motor, the handle being engageable with a replaceable head section having a driveable toothbrush head at one end and a body including a transmission means by which the motor in the handle can be connected to the brush, all disposed along a longitudinal head-handle direction. Commonly the head section has a male plug engagement part at its end opposite to the brush, and the handle is provided with a female engagement socket with which this plug engagement part can engage. Such a plug engagement part and socket commonly also comprise a drive linkage by which the transmission means can be connected to the motor. Specifically, the invention relates to a connection means between such a replaceable head section and a handle.

Electric toothbrushes of this general construction are known, see for example U.S. Pat. No. 6,021,538, GB-A-2 228 861, U.S. Pat. No. 4,827,552, EP-A-0 500 537 (=U.S. Pat. No. 5,289,604) being among many. It is desirable to have a secure but replaceable connection means between the handle and the head section which allows the possibility of a connection of the head section to the handle in a unique predetermined alignment so that the bristles are oriented correctly for use.

It is an object of this invention to provide such a connection means. Other objects will be apparent from the description.

According to this invention an electric toothbrush is provided comprising:

a handle containing an electric drive motor and having an engagement socket for a head section;

a replaceable head section having a driveable toothbrush head and having a plug part which is engageable with the socket;

the plug part has an end surface which when the plug part is engaged with the socket faces generally in the direction of the handle, and the socket has an end surface which faces generally in the direction of the head; wherein:

the end surface of the plug part is resiliently deformable in the handle-head direction under the influence of pressure applied longitudinally to the end surface;

one of either the end surface of the plug part or the end surface of the socket has a convexity thereon projecting along the head-handle direction, and the other has a concavity therein which receives the convexity when the plug part is engaged with the socket.

The construction of the invention facilitates the engagement together of the head section and the handle as the convexity and the concavity engage, with the convexity properly received in the concavity only when the plug part and socket, hence the head section and the handle, are in a unique defined alignment relative to each other. Suitably this alignment is a correct alignment for use of the toothbrush.

The head section is usually an elongate structure having the driveable toothbrush head at one end, and having a plug end part engageable with the socket at the opposite end. The elongate structure may contain a drive shaft to link the motor with the driveable head, and the drive shaft may terminate at the opposite end to the head in a connection part to facilitate connection to the drive motor. The socket may for example include a stub axle to connect with this drive shaft. The plug part of the head section which is engageable with the socket is suitably in the form of a hollow tubular, preferably substantially cylindrical, body defined by a body wall, having an end surface which faces in the direction of the handle, preferably substantially perpendicular to the length direction of the body.

The socket may substantially conform internally to the external shape and dimensions of the plug part of the head section, and for example the end surface of the socket which faces in the direction of the head is preferably also substantially perpendicular to the longitudinal direction.

In a first construction the convexity is on the end surface of the plug part, and the concavity is in the end surface of the socket.

In a second construction the concavity is located in the end surface of the plug part, and the convexity is located in the end surface of the socket.

The end surface of the plug part of the head section may be made resiliently deformable in various ways. For example the body wall adjacent to the end surface may comprise a longitudinally resiliently flexible structure, e.g. it may incorporate parts made of a resilient, e.g. rubbery material, or a flexible resilient bellows structure.

In a preferred construction the end surface of the plug part of the head section is made resiliently deformable by means of an aperture adjacent to the end surface and passing completely through the wall, and which is bounded by a resiliently flexible bridge part partly or preferably wholly bridging the aperture on the side of the aperture adjacent to the end surface, a surface of the bridge part being an end surface of the plug part of the head section, e.g. of the tubular body, the bridge part being resiliently bendable, the convexity in the first construction or the concavity in the second construction being on the end surface of the bridge part.

Such an aperture may be in the form of a slot in the wall of the tubular body. Such a slot may be substantially parallel-sided and typically rectangular over at least part of its length, and with its length direction in the circumferential direction of the plug part, e.g. of the tubular body. One of the long sides of such a rectangular slot is preferably parallel to the end surface of the head section and comprises the bridge part.

Suitably the end surfaces of respectively the plug part and the socket lie substantially in a plane, and the convexity is in the form of a well-defined projection from the plane in which the end surface of the plug part or the socket respectively lies, and the concavity is in the form of a well-defined cavity in the plane in which the end surface of the plug part or the socket respectively lies. The projection on the end surface of respectively the plug part of head section in the first construction or the socket in the second construction may for example be a small bump with sloping ramped side surfaces, e.g. a substantially hemispherical or conical bump. Alternatively the end surface of the plug may be shaped into a projecting salient, e.g. a "V" profiled end surface.

The concavity in the end surface respectively of the socket or the plug part of the head section may conform substantially to the shape and side of the convexity on the end surface respectively of the head section or the socket. A convexity in the form of a small bump as described above, with a correspondingly-shaped concavity can enable the engagement of the plug with the socket in a precise alignment.

Therefore in a first preferred embodiment of the electric toothbrush of the invention, the head section is an elongate structure having the driveable toothbrush head at one end, having a plug end part engageable with the socket at the opposite end, the plug part of the head section which is engageable with the socket is in the form of a hollow, tubular body having an end surface which faces in the direction of the handle and is defined by a body wall, a projection is on the end surface of the plug part, and the concavity is in the end surface of the socket, an aperture is located adjacent to the end surface and passing completely through the body wall, and is bounded by a resiliently flexible bridge part bridging the aperture on the side of the aperture adjacent to the end surface, a surface of the bridge part being an end surface of the plug part of the head section, and the projection is on the end surface of the bridge part.

In a second preferred embodiment of the electric toothbrush of the invention, the head section is an elongate structure having the driveable toothbrush head at one end, having a plug end part engageable with the socket at the opposite end, the plug part of the head section which is engageable with the socket is in the form of a hollow, tubular body having an end surface which faces in the direction of the handle and is defined by a body wall, the projection is on the end surface of the socket, and the concavity is in the end surface of the socket, an aperture is located adjacent to the end surface and passing completely through the body wall, and is bounded by a resiliently flexible bridge part bridging the aperture on the side of the aperture adjacent to the end surface, a surface of the bridge part being an end surface of the plug part of the head section, and the concavity being in the end surface of the bridge part.

With the plug part of the head section in place engaged with the socket the respective end surfaces may be closely adjacent, preferably in contact.

The plug part of the head section and the socket may be provided with engagement features to facilitate a secure locking but releasable engagement of the plug part, and hence the head section, with the socket, and these engagement features may comprise a screw threaded connection or a snap fit connection, among others, such engagement features may be of generally known type.

A bayonet connection is preferred. A bayonet connection is a known type of connection, in which for example a plug part is inserted longitudinally into a female socket, and the adjacent surfaces of the plug part and the socket are provided with engagement parts which engage upon relative rotation of the plug part and socket. Typically the engagement parts of a bayonet connection comprise pairs of respective abutment parts one member of the pair abutting behind the other on rotation, to prevent longitudinal removal of the plug from the socket. If a bayonet connection is used, then the above-mentioned longitudinally resiliently flexible structure, e.g. the aperture is located longitudinally between the end surface of the plug part of the head section and the engagement parts of the plug part.

In the second construction, i.e. in which the concavity is located in the end surface of the end part of the head section, it is preferred that a part of the end surface of the plug part adjacent to the concavity, e.g. circumferentially adjacent to the concavity, preferably comprising a part of the bridge part, comprises a ramp surface, i.e. having a surface aligned at a sloping alignment, i.e. non-perpendicularly, relative to the end surface of the socket and consequently also to the longitudinal direction. Preferably the end surface of the plug part includes a concave region and the ramp surface forms part of such a concave region of the end surface of the plug part. Such a construction facilitates the insertion of the plug part into the socket to the extent that the respective end surfaces of the plug part and socket contact each other, but with the convexity on the end surface of the socket fitting into a gap between the end surface of the plug part and the end part of the socket, bounded by the concave region, e.g. where the sloping surface diverges from the end surface of the socket. Relative rotation of the plug part and the socket, e.g. to engage bayonet connection parts, can then cause the ramp surface to ride over the convexity, and if the ramp surface comprises part of the bridge part can consequently causing the bridge part to resiliently deform as it rides over the convexity. Further rotation then causes the concavity to receive the convexity, and can allow the bridge part to resiliently snap back toward its original shape behind the convexity.

The present invention provides an advantageous connection between the head section and the handle as follows. When the plug part is inserted into the socket the head section may not be in a suitable alignment for use. This is particularly likely if the head section and socket have engagement features which require relative rotation, e.g. a bayonet connection. This causes the convexity and the concavity also to be out of alignment, and causes the convexity to abut against the end surface respectively of the socket or the head section without engaging with the concavity. This abutment applies pressure to the resiliently deformable end surface of the head section e.g. to the bridge part. This pressure causes the bridge part to bend against its resilience, e.g. to arch. As the head section is rotated e.g. to cause engagement means such as a bayonet connection to engage, this rotation brings the head end into an appropriate alignment for use and the convexity and the concavity into alignment so that the resilience causes the convexity to "snap" into the concavity in a way that can be felt, and may even be heard, by the user. This can give the user a clear indication that the head section is properly aligned for use and the engagement parts are correctly aligned and securely engaged.

Additionally the fitting of the convexity into the concavity and the holding therein of the convexity by the resilience of the head end helps to retain the head section securely in place on the handle during the use of the toothbrush, for example against the vibration of the motor or stresses of use in toothbrushing.

Other features of the electric toothbrush of this invention may be conventional. For example, the head section may have a driveable toothbrush head which includes a bristle carrier, which is rotatable or reciprocally oscillatory rotatable about an axis substantially perpendicular to the longitudinal axis of the toothbrush. Such constructions are well known. All or part of such a driveable toothbrush head bristle carrier may itself be replaceable. The handle may include a motor and transmission section, which is capable of driving the drive shaft in rotary motion. The head section may include a transmission system to convert continuous rotary motion of the bristle carrier into oscillatory rotary motion of the bristle carrier. Such transmission systems are known in the art.

The head section and the surfaces of the socket may be made of plastics materials and/or metals common to the art of electric toothbrushes, for example, polypropylene etc.

The term "resilient" as used herein means primarily a part or structure that deforms under applied pressure and rapidly returns substantially to its initial position on removal of the pressure, in the manner of a spring. Many common plastics and rubbery materials used in the manufacture of electric toothbrushes are resilient.

The invention also provides a replaceable head section suitable for use with an electric toothbrush as described herein.

Such a replaceable head section may comprise an elongate structure having a driveable toothbrush head at one end, having a plug end part at the opposite end, the plug part of the head section being in the form of a hollow, tubular body having an end surface and being defined by a body wall, an aperture located adjacent to the end surface and passing completely through the body wall, the aperture being bounded by a resiliently flexible bridge part bridging the aperture on the side of the aperture adjacent to the end surface, a surface of the bridge part being an end surface of the plug part of the head section, and a projection or a cavity on the end surface of the bridge part. Such a plug end part is engageable with the corresponding socket of a toothbrush handle as described herein. Preferred features of such a replaceable head section are as described herein.

For example in such a replaceable head section the plug part of the head section which is engageable with the socket may be in the form of a hollow, tubular body having an end surface which faces in the direction of the handle and is defined by a body wall, an aperture may be located adjacent to the end surface and passing completely through the body wall and bounded by a resiliently flexible bridge part bridging the aperture on the side of the aperture adjacent to the end surface, a surface of the bridge part may be an end surface of the plug part of the head section, the concavity is preferably in the end surface of the bridge part and part of the bridge part comprises a ramp surface at a sloping alignment relative to the longitudinal direction of the head part.

The present invention also provides a toothbrush handle containing an electric drive motor and having an engagement socket suitable for a head section as described herein.

The plastics material parts of the toothbrush of this invention may be made by an injection moulding process in which flexible plastics materials are injected into a mould having a mould cavity which defines the shape and dimensions of one or more component parts of the toothbrush, for example the replaceable head section thereof. Such a process forms a further aspect of this invention.

In a further aspect the invention provides an injection mould having a cavity therein suitable for use in this injection moulding process.

The invention will now be described by way of example only with reference to the accompanying drawings.

FIG. 1 shows overall the schematic layout of an electric toothbrush with a replaceable head section.

FIG. 2A shows a sectional view of a plug part of the toothbrush of the invention.

FIG. 2B shows a side view of the plug part shown in FIG. 2A.

FIG. 2C shows a part sectional view of the end of a toothbrush handle closest to the head section.

FIG. 3A shows a sectional view of a plug part of the toothbrush of the invention inserted into the socket of a toothbrush handle.

FIG. 3B shows the same view as FIG. 3A but with the plug part inserted more deeply into the socket of a toothbrush handle.

FIG. 3C shows the same view as FIG. 3B but with the plug part rotated in the socket.

FIG. 4A shows a plug part inserted into the socket of a toothbrush handle.

FIG. 4B shows the plug part of FIG. 4A rotated through 180 degrees.

FIG. 4C shows a part sectional view of the end of a toothbrush handle closest to the head section.

FIG. 5A–5C show the operation of the construction of FIG. 4 in more detail.

FIG. 5A shows a plug part inserted into the socket of a toothbrush handle.

FIG. 5B shows the same view as FIG. 5A but with the plug part rotated from the position seen in FIG. 5A.

FIG. 5C shows the same view as FIG. 5B but with the plug part rotated from the position seen in FIG. 5B.

Figure 6A:
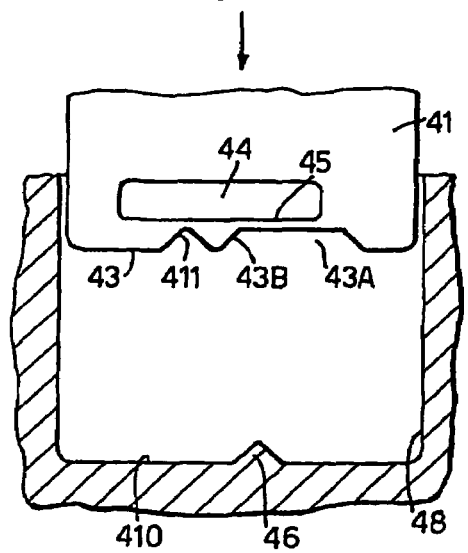
Figure 6B:
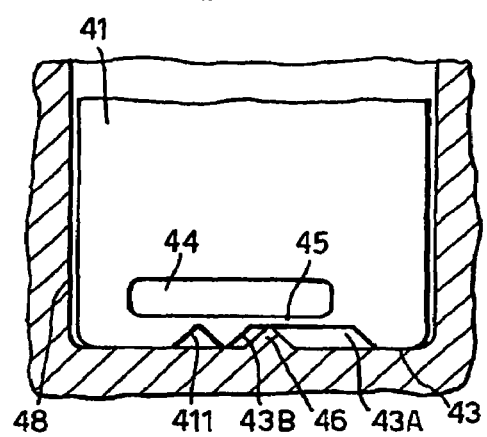
Figure 6C:
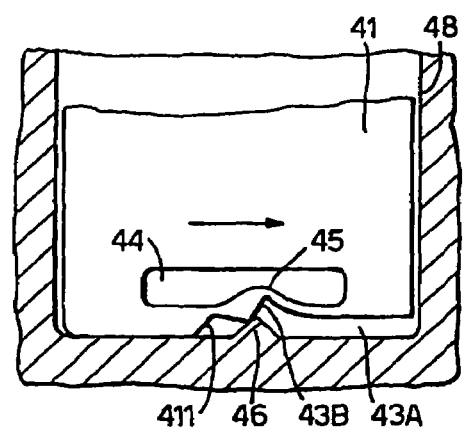
Figure 6D:
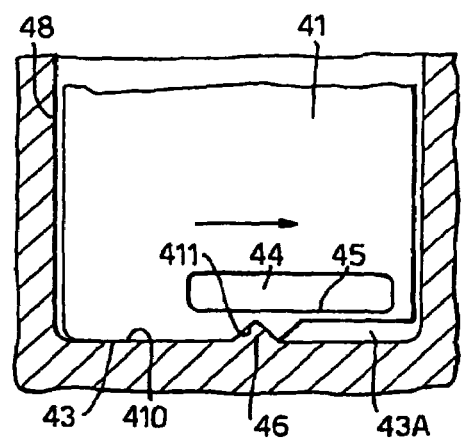

FIG. 6A–6D show another construction similar to FIG. 5. FIG. 6A shows a sectional view of a plug part of the toothbrush of the invention inserted into the socket of a toothbrush handle. FIG. 6B shows the same view as FIG. 6A but with the plug part rotated from the position seen in FIG. 6A. FIG. 6C shows the same view as FIG. 6B but with the plug part rotated from the position seen in FIG. 6B. FIG. 6D shows the same view as FIG. 6D but with the plug part rotated from the position seen in FIG. 6C.

Figure 7A:
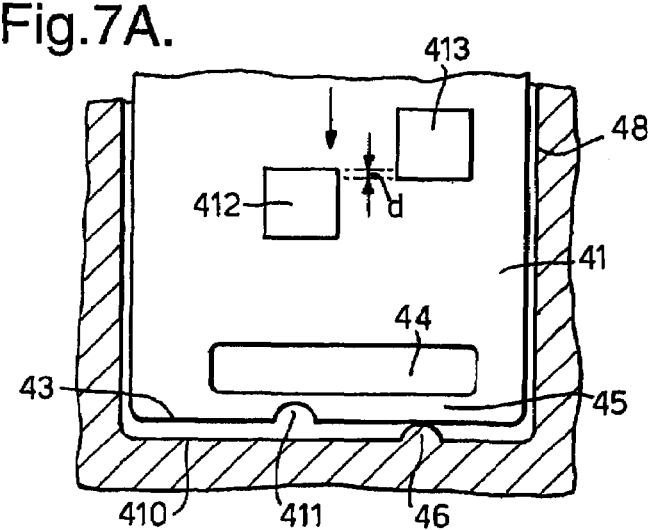
Figure 7B:
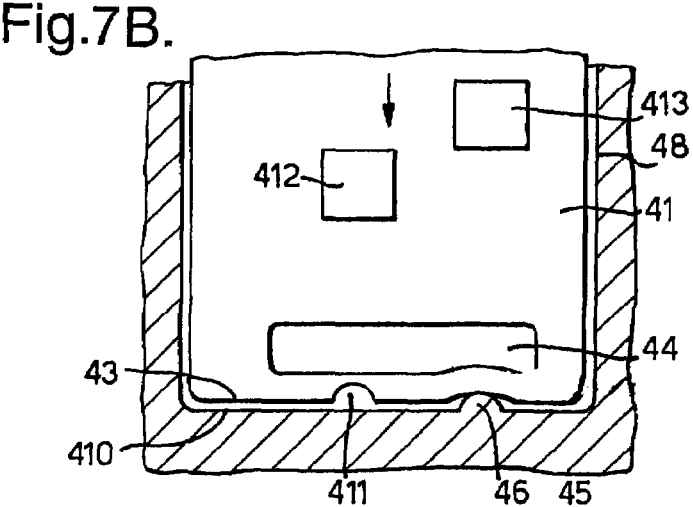
Figure 7C:
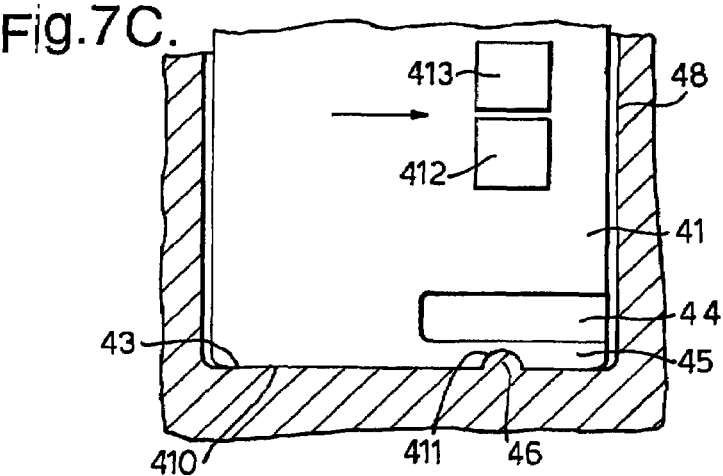

FIG. 7A–7C show an alternative mode of operation of the construction of FIG. 4 in more detail. FIG. 7A shows a sectional view of a plug part of the toothbrush of the invention inserted into the socket of a toothbrush handle. FIG. 7B shows the same view as FIG. 7A but with the plug part rotated from the position seen in FIG. 7A. FIG. 7C shows the same view as FIG. 7B but with the plug part rotated from the position seen in FIG. 7B.

FIG. 1

Referring to FIG. 1 an electric toothbrush is shown overall in side view 10. The toothbrush 10 comprises a handle 11 by which it may be held, and which includes a drive motor, batteries, controls etc. (not shown). The handle 11 is replaceably connected at connection 12 to a replaceable head section 13. The connection 12 is a connection of this invention and is more fully described below. The head section includes a head 14 at the head end of the section 13 remote from handle 11 and a hollow tubular body 15. The body 15 is engageable with the handle 11 at the connection 12. The assembly of handle 11 replaceable section 13 and head 14 are disposed along the head-handle length direction A—A of the toothbrush 10. In the head 14 is mounted a driveable brush 16, from which a cluster of bristles 17 extend in a general bristle direction B—B generally perpendicular to length A—A. The brush 16 is driven by the motor (not shown) via drive shaft 18 (shown generally) extending along inside the hollow tubular body 15. The brush 16 is mounted on an axle (not shown) in head 14 for oscillatory rotation about an axis passing through the centre of the bristle cluster 17 and parallel to the bristle direction B—B.

In use the brush 16 performs an oscillatory, i.e. reversing, rotary motion about an axis of rotation parallel to bristle direction B—B and passing through the center in plan of the cluster of bristles 17, and simultaneously a reciprocal up-down motion along direction B—B. Drive mechanisms are known in the art to achieve such motion.

FIG. 2

Figure 2A:
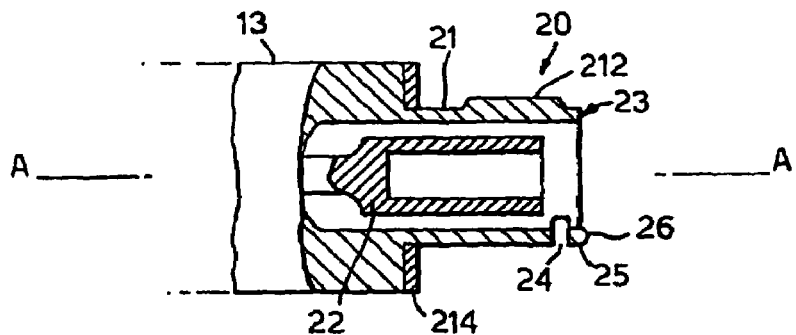
FIGS. 2A–2C show a first construction of the head section and socket of the electric toothbrush of FIG. 1.
Figure 2B:
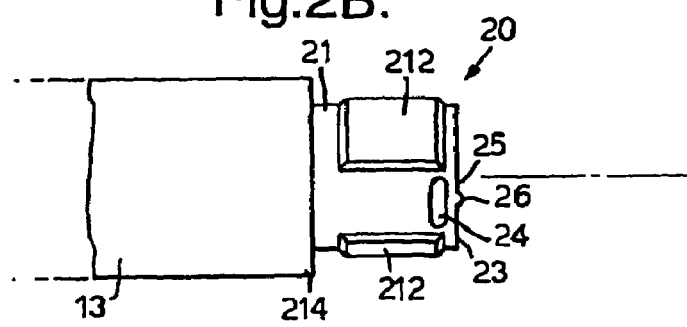

Referring to FIG. 2, the connection 12 of FIG. 1 is shown in more detail. FIG. 2A is a part cutaway part longitudinally sectioned view and FIG. 2B is a side view at ca. 60° rotation about axis A—A to the view in FIG. 2A. FIGS. 2A and 2B show the end of the head section 13 of FIG. 1 closest to handle 10 of FIG. 1 in more detail. The end of the head section 13 closest to the handle comprises a plug part 20 overall comprising a hollow cylindrical tubular body 21 of narrowed cross section relative to the adjacent part of the head section 13 nearer to the head end, and bounded by a cylindrical wall. Within body 21 is a rotatable drive shaft 22 the extreme end of which at the handle end of the head section 13 is shown.

At the end of the head section furthest from the head 14 of FIG. 1, the tubular body 21 terminates in an end surface 23 substantially in a plane perpendicular to the length direction A—A. At this end the tubular body 21 is in the form of a hollow cylinder bounded by thin side walls.

Closely adjacent to end surface 23 there is an aperture 24 in the wall of body 21 extending completely through the wall of body 21. The aperture 24 is in the shape of a substantially rectangular slot, with its length direction substantially perpendicular to the length direction A—A, and parallel to the plane of the end surface 23, and extending in the circumferential direction of the cylindrical body 21. On its long side immediately adjacent to the end surface 23 a thin bridge part 25 bounds the aperture 24 and forms part of the end surface 23. Being made integrally of the plastics material of which the tubular body 21 is made, the bridge part 25 is capable of bending resiliently under the action of pressure applied to it in the longitudinal direction A—A.

On the end surface of the bridge part 25 is a small projection 26 projecting in the longitudinal A—A. Projection 26 is in the shape of a small substantially hem-spherical bump.

Figure 2C:
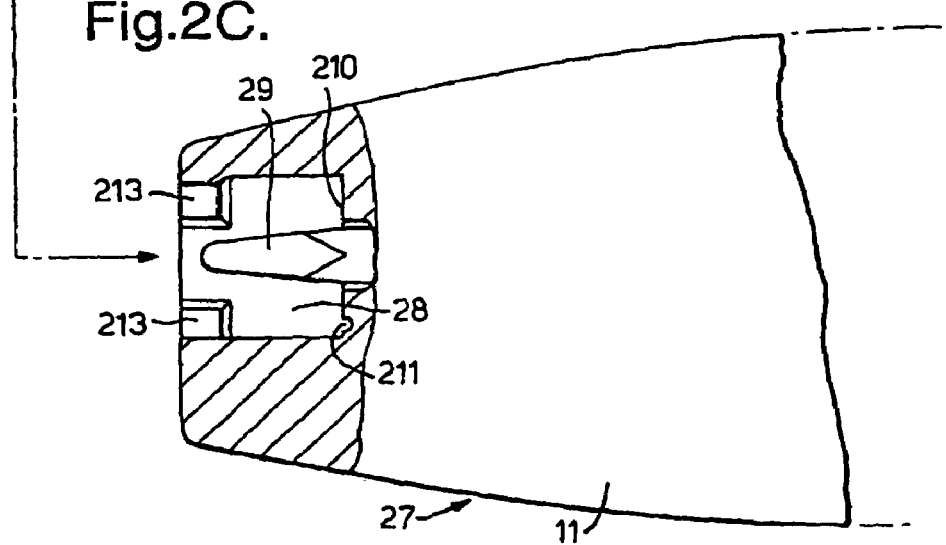

FIG. 2C also shows generally 27 the part of the handle 11 immediately adjacent to the head section 13 of FIG. 1 in a part cutaway part sectioned view. Provided in the part of the handle 11 is an engagement socket 28, facing generally in the direction of the head end of head section 13 and substantially conforming to the external shape and dimensions of the tubular body 21, which is engageable with the socket 28. A stub axle 29 connected to the drive motor (not shown) extends into socket 28. The socket 28 is bounded by side surfaces and by an end surface 210 substantially in a plane perpendicular to the length direction A—A.

In the end surface 210 is a small cavity 211, which corresponds closely in shape to the projection 26. The cavity 211 is positioned such that when the plug part 20 is fully inserted in and engaged with socket 28 and in a unique alignment with the socket 28 the projection 26 fits into cavity 211.

The outer surface of the tubular body 21 and the side surfaces of the socket 28 are further provided with bayonet connection engagement parts 212, 213. Typically three of these are present, arranged at 120° around the tubular body 21 and socket 28. The part of the head section 13 immediately adjacent to the tubular body 21 nearer to the head end is formed as an a resilient collar 214 of rubber material to form a seal between head section 13 and handle 11.

Features 21 and 28 are also shown schematically in FIG. 1.

The construction shown in FIG. 2 works as follows. The tubular body 21 is introduced into the socket 28. The stub axle 29 engages with the end of the drive shaft 22. The tubular body 21 may be inserted into the socket 28. Introduction of the tubular body 21 to the full length of the socket 28 will only be possible when the bayonet connection parts 212, 213 are aligned for introduction of the body 21, i.e. so that parts 212 fit between parts 213, and this alignment will normally initially be with the brush head 14 not in its normal alignment for use. With the body 21 fully inserted into socket 28 the tubular body 21 may then be then rotated about its length axis A—A to cause the engagement parts 212 to move to a position behind, i.e. deeper in the socket 28 than the parts 213. With the parts 212 in position behind parts 213 removal of the plug 20 from socket 28 is prevented. The bayonet connection parts 212, 213 may be shaped in a generally known manner to provide an end stop to further rotation when this alignment is achieved, or the body 21 and/or socket 28 may be otherwise provided with end stop means. Bayonet connections of this general type are known in the art.

FIG. 3

Figure 3A:
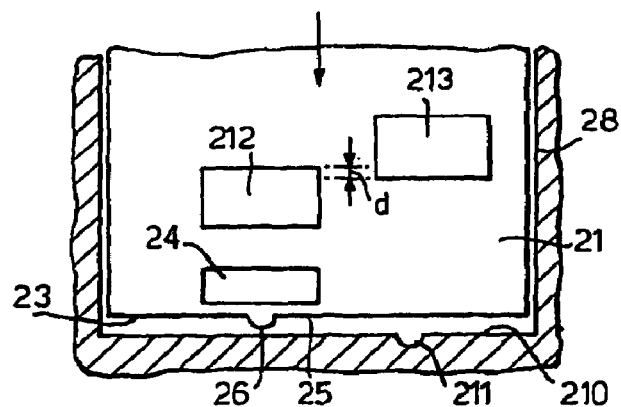
FIGS. 3A–3C show operation of the construction of FIG. 2 in more detail.
Figure 3B:
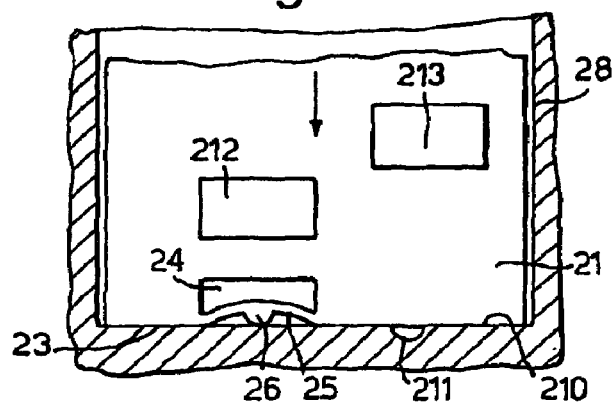
Figure 3C:
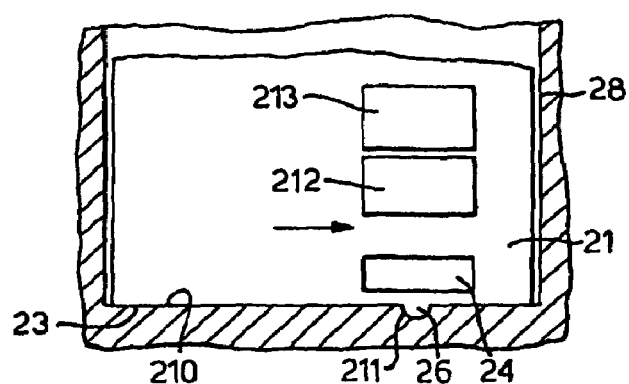

The action of the projection 26 and the cavity 211 are shown more clearly in FIGS. 3A–C. As shown in FIG. 3A, when the tubular body 21 is first inserted into socket 28 in the direction of the arrow, before the head section 13 has been rotated to bring the bayonet connection parts 212, 213 into alignment, the projection 26 and the cavity 211 are not in alignment, and the projection 26 abuts against the end surface 210 of socket 28. Also the parts 212 are not deep enough in the socket 28 to fit behind the parts 213, i.e. the part 212 is misaligned in the longitudinal direction with part 213 by the distance "d". As shown in FIG. 3B, as the body 21 is urged deeper into cavity 28 in the direction of the arrow the abutment of the projection 26 against the surface 210 applies pressure to the projection 26, which is communicated to bridge part 25. This pressure causes the bridge part 25 to bend resiliently, i.e. arching towards the head end of the head section 13. The deformation of the bridge part 25 is sufficient to allow the body 21 to move the distance "d" further into socket 28. As shown in FIG. 3C, as the head section 13 is rotated in the direction of the arrow to bring the bayonet connection parts 212, 213 into alignment with part 212 behind part 213, this rotation brings the projection 26 and the cavity 211 into alignment. End stop features (not shown) may be provided on the body 21 and/or socket 28 to prevent further rotation of the body which might bring the parts 212, 213 out of alignment The resilience of the bridge part 25 causes the projection 26 to "snap" into the cavity 211 in a way that can be felt by the user and may even be heard by the user. This gives the user a clear indication that the bayonet connection engagement parts 212, 213 are correctly aligned and securely engaged. Additionally the fitting of the projection 26 into cavity 211 helps to retain the head section 13 securely in place on the handle during the use of the toothbrush, for example against the vibration of the motor or use stresses.

The collar 214 is compressed between the head section 13 and the handle 11 as the bayonet connection parts 212, 213 engage, and provides tension into the connection 12 to help to hold the head section 13 and handle securely together in addition to providing a seal.

To disengage the head section from the handle the head section 13 is rotated in the reverse direction to that shown in FIG. 3C so as to disengage parts 212, 213. As the projection 26 and cavity 211 are hemispherical in shape their surfaces can smoothly slide over each other in a ramp action, causing the projection 26 to leave cavity 211 and bridge unit 25 again to bend resiliently as the projection 26 leaves cavity 211, and the projection 26 comes into abutment again with the end of surface 210 of the socket 28 in a reverse of FIG. 2. When the tubular body 21 is removed from socket 21 the bridge part 25 springs back into its original undeformed shape as shown in FIG. 1.

FIG. 4

Figure 4A:
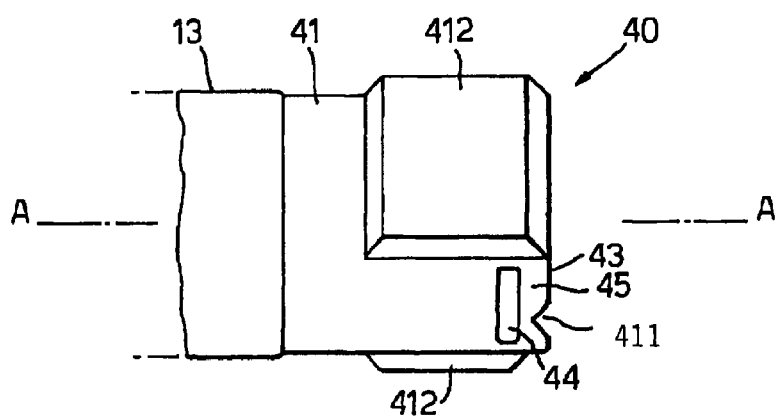
FIG. 4A–4C show a second construction of the head section and handle of the electric toothbrush of FIG. 1.
Figure 4B:
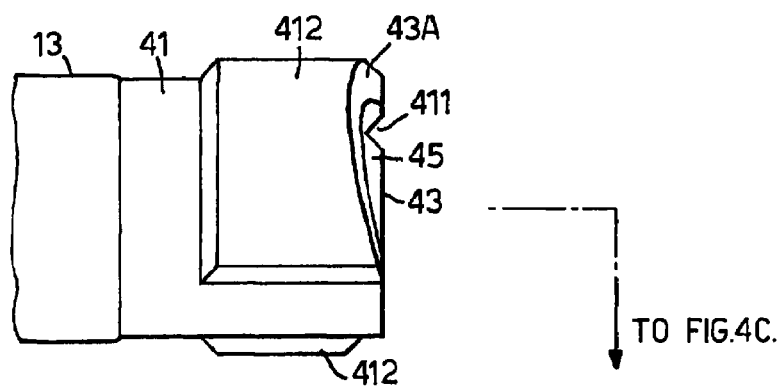

Referring to FIG. 4 the connection 12 of FIG. 1 is shown in more detail in a second construction. FIG. 4A and FIG. 4B are side views at ca. 180° rotation about axis A—A to each other. FIGS. 4A and 4B show the end of the head section 13 of FIG. 1 closest to handle 10 of FIG. 1 in more detail. Features corresponding to FIGS. 2 and 3 are numbered with corresponding reference numerals (e.g. feature 41 of FIG. 4 corresponds to feature 21 of FIG. 2).

Closely adjacent to end surface 43 of the tubular body 41, there is an aperture 44 in the wall of the tubular body 41, in the shape of an elongated substantially rectangular slot with its length direction perpendicular to the length direction A—A of the head section. On its long side adjacent to end surface 43 a thin bridge part 45 bounds the aperture 44. In the bridge part 45 there is a small cavity 411 in the form of a wedge shaped notch in the bridge part 45. Part of the end surface 43 is in a plane substantially perpendicular to the length direction A—A and part 43A of the end surface 43 is aligned at a sloping alignment relative to this plane.

Figure 4C:
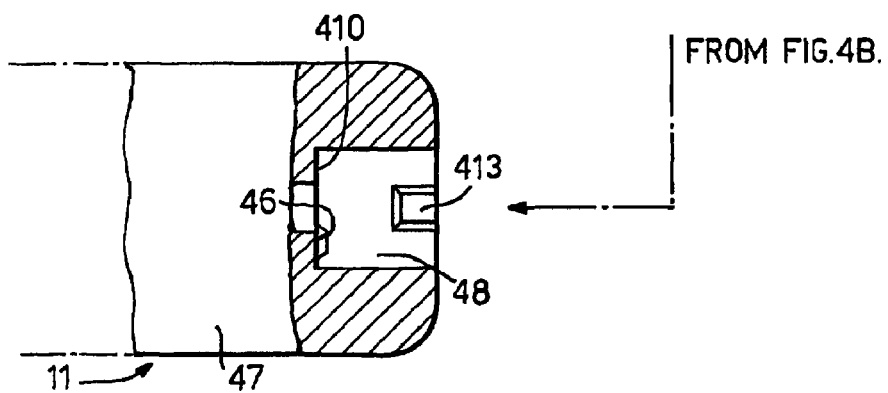

FIG. 4C also shows generally 47 the part of the handle 11 of this second construction immediately adjacent to the head section 13 of FIG. 1 in a part cutaway part sectioned view. In the part of the handle 11 is an engagement socket 48, facing generally in the direction of the head end of head section 13 and substantially conforming to the external shape and dimensions of the tubular body 41, which is engageable with the socket 48. FIG. 4C is for convenience drawn at a smaller scale to FIGS. 4A and 4B. A stub axle (not shown) connected to the drive motor (not shown) extends into socket 48. The socket 48 is bounded by side surfaces and by an end surface 410 substantially perpendicular to the length direction A—A.

On the end surface 410 is a convexity being a small wedge-shaped projection 46, which corresponds closely in shape to the cavity 411. The projection 46 is positioned such that when the plug part 40 is fully inserted in and engaged with socket 48 and in a unique alignment with the socket 48 the projection 46 fits into concavity 411.

The outer surface of the tubular body 41 and the side surfaces of the socket 48 are further provided with bayonet connection engagement parts respectively 412, 413. Typically three of these are present, arranged at 120° around the tubular body 41 and socket 48.

Features 41 and 48 are also shown schematically in FIG. 1.

The construction shown in FIG. 4 works analogously to FIG. 2. The tubular body 41 is introduced into the socket 48, and the bayonet connection parts 412, 413 operate as described with reference to FIG. 2.

FIG. 5

The action of the projection 46 and the concavity 411 are shown more clearly in FIGS. 5A–C. As shown in FIG. 5A, when the tubular body 41 is first inserted into socket 48 in the direction of the arrow, before the head section 13 (not shown in FIG. 5) has been rotated to bring the bayonet connection parts 412, 413 into alignment, the projection 46 and the concavity 411 are not in alignment. However the sloping part 43A of the end surface 43 and the end surface 410 of the socket define a space between them, into which projection 46 fits, with the surfaces 43 and 410 in contact (a slight gap is shown for clarity). As shown in FIG. 5B, as the body 41 is rotated in the direction of the arrow, the part 43A rides over the projection 46 in a ramp action, compressing the bridge part 45, which bends resiliently, i.e. arching towards the head end of the head section 13. The part 43A therefore comprises a ramp surface circumferentially adjacent to the concavity 411.

As shown in FIG. 5C, as the head section 13 is rotated in the direction of the arrow to bring the bayonet connection parts 412, 413 into alignment with part 412 behind part 413, this rotation brings the projection 46 and the cavity 411 into alignment. End stop features (not shown) may be provided on the body 41 and/or socket 48 to prevent further rotation of the body which might bring the parts 412, 413 out of alignment. The resilience of the bridge part 45 causes the cavity 411 to "snap" around projection 46 in a way that may be felt by the user and may even be heard by the user. This gives the user a clear indication that the bayonet connection engagement parts 412, 413 are correctly aligned and securely engaged. Additionally the fitting of the projection 46 into concavity 411 helps to retain the head section 13 securely in place on the handle during the use of the toothbrush, for example against the vibration of the motor or use stresses.

Disengagement of the head section from the handle in the construction shown in FIGS. 5A–C is, analogously with FIG. 3, a reverse of the above described operation.

FIG. 6

Referring to FIGS. 6A–D the construction and operation of another embodiment of the head section 13 (not shown in FIG. 6) is illustrated. Parts corresponding to FIG. 5 are numbered correspondingly. The action of the projection 46 and the concavity 411 are shown. As shown in FIG. 6A, when the tubular body 41 is first inserted into socket 48 the projection 46 and the cavity 411 are not in alignment. However as shown in FIG. 6B the part 43A of the end surface 43 is a concave region, analogous to the region 43A of FIG. 5, and the concave region 43A and the end surface 410 of the socket define a space between them, into which projection 46 fits, with the surfaces 43 and 410 in contact (a slight gap is shown for clarity). Circumferentially adjacent to concavity 411 the surface 43A forms a ramp surface 43B. As shown in FIG. 6C, as the body 41 is rotated within the socket 48 in the direction of the arrow, the ramp surface 43B rides over the projection 46 in a ramp action, compressing the bridge part 45, which bends resiliently, i.e. arching towards the head end of the head section 13.

As shown in FIG. 6D, continued rotation of the head section 13 in the direction of the arrow this brings the projection 46 and the cavity 411 into alignment, so the bridge part 45 snaps back into its original position. The embodiment shown in FIG. 6 may be provided with bayonet connection parts and end stop means in a manner analogous to FIG. 5.

Disengagement of the head section from the handle in the construction shown in FIGS. 6A–D is, analogously with FIG. 5, a reverse of the above described operation.

FIG. 7

The action of the projection 46 and the cavity 411 in a modified construction of FIG. 4 are shown more clearly in FIGS. 7A–C. This illustrates a modification of FIG. 4 in which the sloping part 43A of the end surface 43 is absent, i.e. the end surface 43 lies in a plane perpendicular to the length direction A—A. As shown in FIG. 7A, when the tubular body 41 is first inserted into socket 48 in the direction of the arrow, before the head section 13 has been rotated to bring the bayonet connection parts 412, 413 into alignment, the projection 46 and the cavity 411 are not in alignment, and the projection 46 abuts against the end bridge part 45. Also the parts 412 are not deep enough in the socket 48 to fit behind the parts 413, i.e. the part 412 is misaligned in the longitudinal direction with part 413 by the distance "d". As shown in FIG. 7B, as the body 41 is urged deeper into cavity 48 in the direction of the arrow the abutment of the projection 46 against the bridge part 45 applies pressure to the part 45 bends resiliently, i.e. arching towards the head end of the head section 13. The deformation of the bridge part 45 is sufficient to allow the body 41 to move the distance "d" further into socket 48. As shown in FIG. 7C, as the head section 13 is rotated in the direction of the arrow to bring the bayonet connection parts 412, 413 into alignment with part 412 behind part 413, this rotation brings the projection 46 and the cavity 411 into alignment. End stop features (not shown) may be provided on the body 41 and/or socket 48 to prevent further rotation of the body which might bring the parts 412, 413 out of alignment. The resilience of the bridge part 45 causes the bridge part 45 to "snap" back into its original shape so that cavity 411 fits around projection 46 in a way that may be felt by the user and may even be heard by the user. This gives the user a clear indication that the bayonet connection engagement parts 412, 413 are correctly aligned and securely engaged. Additionally the fitting of the projection 46 into cavity 411 helps to retain the head section 13 securely in place on the handle during the use of the toothbrush, for example against the vibration of the motor or use stresses.

Disengagement of the head section from the handle in the construction shown in FIGS. 7A–C is, analogously with FIGS. 3 and 5, a reverse of the above described operation.

The invention claimed is:

1. A toothbrush comprising:
   a handle containing an electric drive motor and having an engagement socket for a head section;
   a replaceable head section being an elongate structure having a driveable toothbrush head at one end and having a plug part which is engageable with the socket at its opposite end;
   the plug part having an end surface which when the plug part is engaged with the socket faces generally in the direction of the handle, and the socket having an end surface which faces generally in the direction of the head; wherein:
   the end surface of the plug part is resiliently deformable in the handle-head direction under the influence of pressure applied longitudinally to the end surface;
   one of either the end surface of the plug part or the end surface of the socket has a convexity thereon projecting along the head-handle direction, and the other has a concavity therein which receives the projection when the plug part is engaged with the socket.

2. A toothbrush according to claim 1 wherein the convexity is on the end surface of the plug part, and the concavity is located in the end surface of the socket.

3. A toothbrush according to claim 1 wherein the concavity is located in the end surface of the plug part, and the convexity is located on the end surface of the socket.

4. A toothbrush according to claim 3 wherein:
   the plug part of the head section which is engageable with the socket is in the form of a hollow, tubular body having an end surface which faces in the direction of the handle and is defined by a body wall, an aperture is located adjacent to the end surface and passes completely through the body wall and is bounded by a resiliently flexible bridge part bridging the aperture on the side of the aperture adjacent to the end surface, a surface of the bridge part is an end surface of the plug part of the head section, the concavity is in the end surface of the bridge part and part of the bridge part comprises a ramp surface at a sloping alignment relative to the longitudinal direction of the head section, a concave region is provided on the end surface of the plug part, the ramp surface comprising part of the concave region of the end surface of the plug part, and when the plug part is inserted into the socket the convexity on the end surface of the socket fits into a gap between the end surface of the plug part and the end surface of the socket bounded by the concave region, relative rotation of the plug part and the socket causes the ramp surface to ride over the convexity, and further relative rotation then causes the concavity to receive the convexity.

5. A toothbrush according to claim 1 wherein the concavity in the end surface respectively of the socket or the plug part of the head conforms substantially to the shape and size of the convexity on the end surface respectively of the plug part or the socket.

6. A toothbrush according to claim 1 wherein the plug part and socket are provided with engagement features to facilitate a secure but releasable engagement of the plug part with the socket.

7. A replaceable head section for a toothbrush being an elongate structure having a driveable toothbrush head at one end and having a plug part at its longitudinally opposite end, wherein the plug part is in the form of a hollow, tubular body defined by a body wall and having an end surface, wherein the end surface of the plug part is resiliently deformable in the longitudinal direction under the influence of pressure applied longitudinally to the end surface and the end surface of the plug part has a convexity thereon projecting along the longitudinal direction, or a concavity therein.

8. A replaceable head section according to claim 7 wherein the end surface of the plug part of the head section is made resiliently deformable by means of an aperture adjacent to the end surface and passing completely through the body wall, and which is bounded by a resiliently flexible bridge part partly or wholly bridging the aperture on the side of the aperture adjacent to the end surface, a surface of the bridge part being an end surface of the plug part of the head section.

9. A replaceable head section according to claim 8 wherein the aperture is in the form of a slot having its length direction in the circumferential direction of the plug part.

10. A replaceable head section according to claim 8 wherein the convexity is on the end surface of the bridge part.

11. A replaceable head section according to claim 10 wherein the plug part of the head section is provided with bayonet connection engagement features to facilitate a locking but releasable engagement of the plug part with corresponding bayonet connection features in a socket.

12. A replaceable head section according to claim 8 wherein the concavity is in the end surface of the bridge part.

13. A replaceable head section according to claim 12, wherein there is a ramp surface on the end surface of the plug part adjacent to the concavity.

14. A replaceable head section according to claim 13, wherein the ramp surface comprises part of the bridge part circumferentially adjacent to the concavity.

15. A replaceable head section according to claim 13 wherein the ramp surface comprises part of a concave region of the end surface of the plug part.

16. A replaceable head section for a toothbrush according claim 8 wherein a concavity is in the end surface of the bridge part and part of the bridge part comprises a ramp surface at a sloping alignment relative to the longitudinal direction of the head section.

* * * * *